United States Patent
Guo et al.

(10) Patent No.: US 11,959,122 B2
(45) Date of Patent: Apr. 16, 2024

(54) METHOD FOR ASSESSING MICROBIAL DRUG RESISTANCE MULTI-LEVEL RISKS OF ANTIBIOTIC RESIDUES IN WATER ENVIRONMENT

(71) Applicants: Nanjing Institute of Environmental Sciences, MEE, Nanjing (CN); Nanjing University, Nanjing (CN)

(72) Inventors: Xinyan Guo, Nanjing (CN); Na Wang, Nanjing (CN); Qingbin Yuan, Nanjing (CN); Ni Ni, Nanjing (CN); Xiaohui Zhang, Nanjing (CN); Mali Shi, Nanjing (CN); Jingbiao Li, Nanjing (CN)

(73) Assignees: NANJING INSTITUTE OF ENVIRONMENTAL SCIENCES, MEE, Nanjing (CN); NANJING UNIVERSITY, Nanjing (CN)

( * ) Notice: Subject to any disclaimer, the term of this patent is extended or adjusted under 35 U.S.C. 154(b) by 0 days.

(21) Appl. No.: 18/324,954

(22) Filed: May 27, 2023

(65) Prior Publication Data
US 2023/0392183 A1    Dec. 7, 2023

(30) Foreign Application Priority Data
Jun. 1, 2022  (CN) .......................... 202210618679.5

(51) Int. Cl.
| | | |
|---|---|---|
| *C12Q 1/04* | (2006.01) | |
| *A61K 47/68* | (2017.01) | |
| *A61P 31/04* | (2006.01) | |
| *C12Q 1/689* | (2018.01) | |

(52) U.S. Cl.
CPC ............ *C12Q 1/04* (2013.01); *A61K 47/6809* (2017.08); *A61P 31/04* (2018.01); *C12Q 1/689* (2013.01)

(58) Field of Classification Search
CPC .......... C12Q 1/689; C12Q 1/04; A61P 31/04; A61K 47/6809
See application file for complete search history.

(56) References Cited

FOREIGN PATENT DOCUMENTS

| | | |
|---|---|---|
| CN | 105112497 A | 12/2015 |
| CN | 110869511 A | 3/2020 |
| CN | 112877396 A | 6/2021 |
| CN | 106661606 B | 12/2021 |
| CN | 114509420 A | 5/2022 |

OTHER PUBLICATIONS

Wang, Yifan, et al. "Source-specific risk apportionment and critical risk source identification of antibiotic resistance in Fenhe River basin, China." Chemosphere 287 (2022): 131997. (Year: 2022).*
Dorival-García, Noemí, et al. "Simultaneous determination of 13 quinolone antibiotic derivatives in wastewater samples using solid-phase extraction and ultra performance liquid chromatography-tandem mass spectrometry." Microchemical Journal 106 (2013): 323-333. (Year: 2013).*
Fenhe River (retrieved from https://en.wikipedia.org/wiki/Fen_River on Sep. 26, 2023). (Year: 2023).*
Notification to Grant Patent Rights for Invention, issued in Chinese priority application No. 202210618679.5, dated Mar. 26, 2023.
Patent Search Report, prepared by Beijing Zhanqiao Patent Agency, dated Jun. 1, 2022.

* cited by examiner

*Primary Examiner* — Robert J Yamasaki
*Assistant Examiner* — Trevor Kane
(74) *Attorney, Agent, or Firm* — WPAT, PC

(57) ABSTRACT

A method for assessing microbial drug resistance multi-level risks of antibiotic residues in water environments, belonging to the technical field of water environment assessment, comprises the following steps: S1, environment monitoring; S2, preliminary screening of antibiotics: S2-1, determination of n-octanol/water partition coefficient, and S2-2, determination of antibiotic environment concentration; S3, assessment of microbial drug resistance; and S4, high-level assessment. The assessment method of the present disclosure conducts a step-by-step assessment of target antibiotics or target antibiotic derivatives in water environment with risks.

9 Claims, 2 Drawing Sheets

METHOD FOR ASSESSING MICROBIAL DRUG RESISTANCE MULTI-LEVEL RISKS OF ANTIBIOTIC RESIDUES IN WATER ENVIRONMENT

REFERENCE TO RELATED APPLICATIONS

The present application claims the priority of Chinese patent application No. 202210618679.5, filed on 2022 Jun. 1, the entire disclose of which is incorporated herein by reference.

TECHNICAL FIELD OF THE INVENTION

The present disclosure relates to the technical field of water environment assessment, particularly to a method for assessing microbial drug resistance multi-level risks of antibiotic residues in water environment.

BACKGROUND OF THE INVENTION

Antibiotics refer to a class of secondary metabolites produced by microbes (including bacteria, fungi and *Actinomyces*) or higher animals and plants in the course of life that have resistance to pathogens or other activities, and are chemical substances that can interfere with other cell development functions. Antibiotics commonly used in clinic include extracts from microbial culture solutions and compounds synthesized or semi-synthesized through chemical methods.

Antibiotics play a role in treating infections by killing bacteria. As widely existing organisms, bacteria can also obtain resistance to antibiotics in various forms to escape the killing danger. This resistance is called "bacterial drug resistance", and bacteria having drug resistance are called "drug-resistant bacteria".

Ecological risk refers to the possibility of an ecosystem being affected by all factors except the ecosystem that pose a threat to the ecosystem, and refers to the potential effects of adverse effects such as chemical emissions, human activities and natural disasters on the ecosystem and its components within a certain area. These effects may lead to damage to the structure and function of the ecosystem, thereby endangering the safety and health of the ecosystem.

In people's production and daily life, risk is brought to water environments in various forms. However, there has been no suitable risk assessment method for ecological risk assessment of antibiotics in water environment. Patent CN109146242A discloses a dietary risk assessment method for antibiotic residues in aquaculture aquatic products, which belongs to the technical field of aquatic product quality and safety risk assessment. By establishing a group of dietary risk influencing factors and an assessment group of dietary risk levels, original data is scored according to the grading table of each dietary risk influencing factor, and then brought into a mathematical model to obtain dietary risk scores. The risk level is determined using score classification. The present disclosure constructs an algorithm by through indicators such as aquaculture water environment, aquaculture organisms, antibiotic resistance, and aquatic product consumption for characterization and quick assessment of dietary risk levels. Such the method is conducive to clarifying the monitoring priorities for the use of antibiotics in aquaculture in China in the future, and providing technical support for aquaculture farmers, fisheries regulatory authorities and others to manage the quality and safety of aquatic products.

However, no further research has been conducted on a relationship between antibiotic risk assessment and microbes.

SUMMARY OF THE INVENTION

For the above existing problems, the present disclosure provides a method for assessing microbial drug resistance multi-level risks of antibiotic residues in water environment.

The technical solution of the present disclosure is as follows:

Provided is a method for assessing microbial drug resistance multi-level risks of antibiotic residues in water environment, comprising the following steps:

S1, environment monitoring:

S1-1: background survey on production, use and emission of antibiotics in a target watershed is carried out, a target antibiotic monitoring list is established for ecological risk assessment, and environment monitoring of target antibiotics is then carried out;

S1-2: target antibiotic derivative monitoring is carried out on the target watershed, a target antibiotic derivative monitoring list also needs to be established if byproduct reaction or biotransformation of target antibiotic occurs, and then environment monitoring of target antibiotics is carried out;

S2, preliminary screening of antibiotics: the target antibiotics of the target watershed obtained in step S1-1 and the target antibiotics of the target watershed obtained in step S1-2 are preliminarily screened, step S3 for microbial drug resistance assessment is carried out for further assessment if any one of S2-1 to S2-2 is met, or else the assessment is terminated;

S2-1, determination of n-octanol/water partition coefficient: the n-octanol/water partition coefficient Kow of the target antibiotic or target antibiotic derivative is calculated, and the logarithmic value of the obtained n-octanol/water partition coefficient Kow with a base of 10 is calculated, when 1 g Kow≥3.5, the target antibiotic or target antibiotic derivative has strong liposolubility, and then step S3 for microbial drug resistance assessment is carried out for further assessment;

S2-2, determination of antibiotic environment concentration: the environment concentration MEC of the target antibiotic or target antibiotic derivative is measured, the target antibiotic or target antibiotic derivative has a sustained input source when the environment concentration MEC≥10, and then step S3 for microbial drug resistance assessment is carried out for further assessment;

S3, microbial drug resistance assessment: the drug resistance risk of microbial flora in the target watershed is characterized by using drug resistance risk quotient value $RQ_R$, which is represented by the following formula:

$$RQ_R = MEC/PNEC_R;$$

in the formula, MEC is the environment concentration of the target antibiotic or target antibiotic derivative measured in step S2-2, $PNEC_R$ is a drug resistance prediction invalid concentration of microbial flora in the target watershed, which is represented by the following formula:

$$PNEC_R = MIC/AF;$$

in the formula, MIC is a minimum inhibitory concentration of microbial flora in the target watershed, AF is a dimensionless assessment factor, the minimum inhibitory concentration (MIC) of the microbial flora in the target watershed is determined through EUCAST database, thereby obtaining the drug resistance prediction invalid concentration ($PNEC_R$) of the microbial flora in the target watershed;

the drug resistance risk level of the microbial flora in the target watershed is divided into 4 grades according to the size of $RQ_R$ value: no risk is $RQ_R<0.01$, low risk is $0.01<RQ_R<0.1$, medium risk is $0.1<RQ_R<1$ and high risk is $RQ_R>1$, the drug resistance risk level of the microbial flora in the target watershed is high when $RQ_R>0.1$, and then step S4 for high-level assessment is carried out for further assessment, or else the assessment is terminated;

S4, high-level assessment:

S4-1, extraction of environmental microbes: 50 weight parts of water samples in the target watershed are collected and then filtered through a filter membrane, the filter membrane is cut into fragments with an area of 15-28 mm² after filtration, the fragments together with a phosphate buffer solution that is 1.2-1.5 times of the fragments in volume are put into a container, and then glass beads that are 2.5-3 times of the fragments in volume are added into the container, vortex oscillation is carried out for 15-20 min, and then the filter membrane and the glass beads are removed by filtration to obtain bacterial solution supernatant for later use;

S4-2, gradient concentration culture of antibiotics: the bacterial solution supernatant obtained in step S4-1 is respectively added into 5-6 sterilized conical flasks, 3 glass slides are put into each conical flask for stimulating biological membrane development of sediments, 0.2-0.5 weight part of LB culture medium is added, and then target antibiotics or target antibiotic derivatives with different concentrations that are 0, 0.01 μg/L, 0.1 μg/L, 1 μg/L, 10 μg/L and 100 μg/L respectively are added into the 5-6 different sterilized conical flasks, and then oscillatory reaction is carried out for 14 days at room temperature of 28-33° C. to obtain a target solution;

S4-3, DNA extraction: target solution DNA in the target solution obtained in step S4-2 is extracted while collecting bacteria on the glass slides in the sterilized conical flasks to the phosphate buffer solution to extract bacterial DNA;

S4-4, determination of resistant genes: resistant genes corresponding to the target antibiotics or target antibiotic derivatives are determined, the abundance of the target solution DNA or bacterial DNA is determined to calculate the average relative abundance P of the resistant gene, and meanwhile the average relative abundance $P_0$ of the resistant gene before step S4 is calculated is calculated, and selectivity coefficient S is calculated, which is represented by the following formula:

$$S=ln(P/P_0)$$

S4-5, model fitting: antibiotic concentration C is taken as a horizontal ordinate, and the selectivity coefficient S corresponding to the target solution DNA or bacterial DNA is taken as a longitudinal ordinate, and fitting is carried out by using logistic model. When S=0, the corresponding antibiotic concentration C is the MSC value. The MSC values of the target solution DNA or bacterial DNA are compared, and the smaller MSC value is taken as control basis. This MSC value indicates that microbes carrying drug-resistant genes cannot be enriched under antibiotic conditions being higher than the antibiotic concentration C, so that the relative abundance of drug-resistant genes in the microbial flora is increased.

Further, the target watershed includes a river basin, a sea area and a water functional area. Microbial drug resistance high-level risk study assessment can be carried out on water environments such as rivers, oceans and watersheds.

Further, the microbial flora in the step S3 includes bacteria, fungi or *Actinomyces*, which are all typical microbes in water environments, and have certain representativeness.

Further, the step S3 further comprises environment persistence assessment: the half-life period $t_{1/2}$ of the target antibiotics or target antibiotic derivatives is obtained by database querying combined with model prediction, an environment persistence level is divided into 3 grades according to the size of the half-life period $t_{1/2}$: non persistence is $t_{1/2}<60d$, persistence is $60d<t_{1/2}<180d$, and high persistence is $t_{1/2}>180d$; when $t_{1/2}>60$, the target antibiotics or target antibiotic derivatives have environment persistence, so regardless of the drug resistance risk $RQ_R$ value of the microbial flora in the target watershed, step S4 is carried out for further assessment. Combination of environment persistence with microbial drug resistance can make the assessment method more precise. When the target antibiotics or target antibiotic derivatives are not only persistent but also drug-resistant, it is needed to carry out high-level risk assessment. If the target antibiotics or target antibiotic derivatives are not persistent but drug-resistant, it is needed to timely carry out high-level risk assessment.

Further, the pore diameter of the filter membrane in the step S4-1 is 0.2-0.3 μm, which is beneficial to obtaining bacteria in water samples.

Further, the phosphate buffer solution in the step S4-1 and S4-3 comprises 10 g/L of NaCl solution, 0.25 g/L of KCl solution, 1.6 g/L of Na2HPO4 solution, 0.3 g/L of KH2PO4 solution and the balance of water, and the pH of the phosphate buffer solution is 7.4. This phosphate buffer solution is well compatible to bacteria.

Further, the LB culture medium in the step S4-1 comprises 10 g/L of tryptone, 5 g/L of yeast powder, 10 g/L of sodium chloride and the balance of water. This LB culture medium can effectively culture the bacteria.

Further, in the step S4-4, 2-20 resistant genes are selected.

Further, in the step S3, the dimensionless assessment factor AF is 10.

The present disclosure has the beneficial effects:

(1) The a step-by-step assessment of target antibiotics or target antibiotic derivatives with risks is conducted by using the multi-level risk assessment method for microbial drug resistance of antibiotic residues in the water environment of the present disclosure. Firstly, the target antibiotics or target antibiotic derivatives are preliminarily screened, and the target antibiotics or target antibiotic derivatives are subjected to microbial drug resistance assessment for next-step assessment if meeting the conditions, and high-level risk assessment or assessment termination is continued to be carried out based on different drug resistances so as to finally obtain minimum inhibitory concentration (MSC) values which indicate that microbes carrying drug-resistant genes can be enriched under antibiotic conditions being higher than corresponding antibiotic concentration C so that the relative abundance of drug-resistant genes in microbial flora is increased.

(2) The multi-level risk assessment method for microbial drug resistance of antibiotic residues in the water environment of the present disclosure also combines environmental persistence with microbial drug resistance to make the assessment method more precise. If the target antibiotics or target antibiotic derivatives are not only persistent but also drug-resistant, high-risk assessment must be carried out. If the target antibiotics or target antibiotic derivatives are not persistent but resistant, high-level risk assessment is properly carried out.

(3) The multi-level risk assessment method for microbial drug resistance of antibiotic residues in the water environment of the present disclosure accurately measures the MSC value through experimental methods, with antibiotic concentration C as the horizontal ordinate and the selectivity coefficient S corresponding to the target solution DNA or bacterial DNA as the longitudinal ordinate. A logistic model is used for fitting to obtain the MSC value of the target solution DNA or bacterial DNA, and the smaller MSC value is taken as the control basis.

(4) The assessment results obtained by the multi-level risk assessment method for microbial drug resistance of antibiotic residues in water environment of the present disclosure play an important role in continuous monitoring, source analysis and source control of the water environment. Based on the assessment results, administrative measures such as investigation and rectification within a specified period can be adopted for pollution caused by point sources. For pollution caused by point sources, high ecological risk antibiotic types can be restricted or prohibited in relevant regions.

DETAILED DESCRIPTION

Example 1

Figure 1:
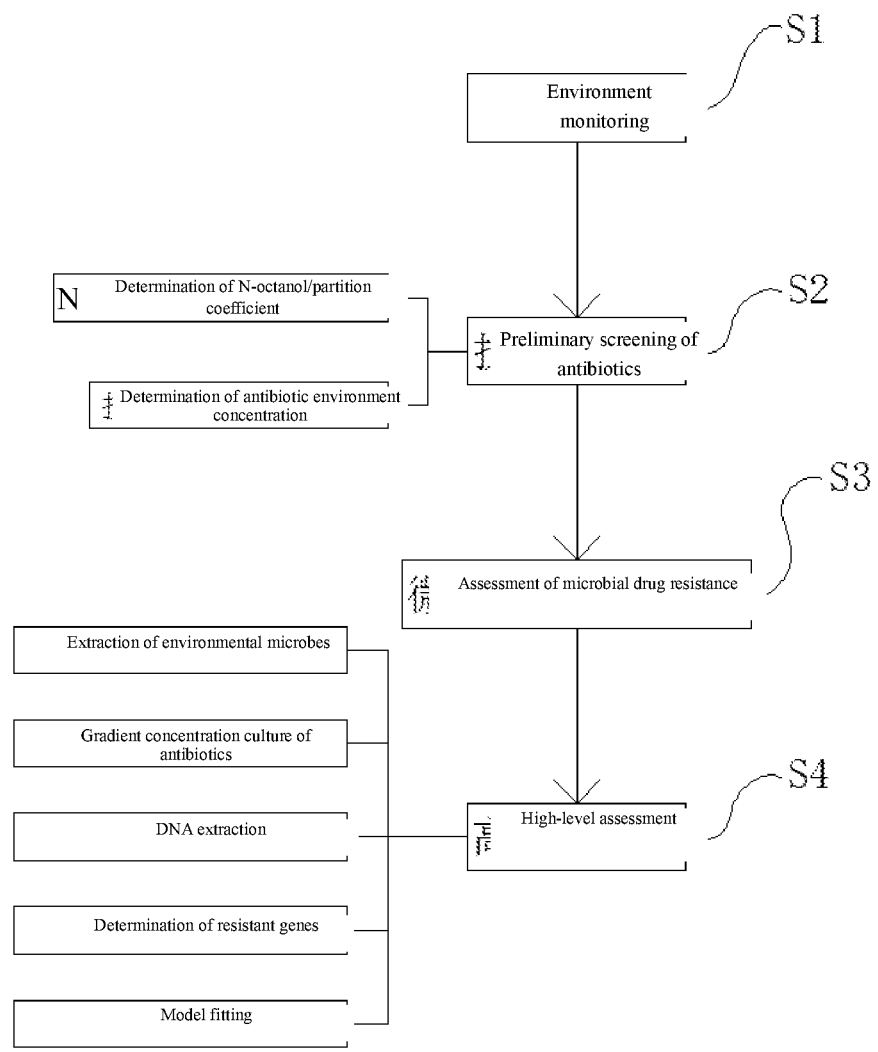
FIG. 1 is a flowchart of a method according to the present disclosure.

A method for assessing microbial drug resistance multi-level risks of antibiotic residues in water environment comprises the following steps:

S1, environment monitoring:

S1-1: background survey on production, use and emission of antibiotics in a target watershed was carried out, a target antibiotic monitoring list was established for ecological risk assessment, and environment monitoring of target antibiotics was then carried out;

S1-2: target antibiotic derivative monitoring was carried out on the target watershed, a target antibiotic derivative monitoring list also needed to be established if byproduct reaction or biotransformation of target antibiotic occurs, and then environment monitoring of target antibiotics was carried out;

S2, preliminary screening of antibiotics: the target antibiotics of the target watershed obtained in step S1-1 and the target antibiotics of the target watershed obtained in step S1-2 were preliminarily screened, step S3 for microbial drug resistance assessment was carried out if any one of S2-1 to S2-2 was met, or else the assessment was terminated;

S2-1, determination of n-octanol/water partition coefficient: the n-octanol/water partition coefficient Kow of the target antibiotic or target antibiotic derivative was calculated, and the logarithmic value of the obtained n-octanol/water partition coefficient Kow with a base of 10 was calculated, the target antibiotic or target antibiotic derivative was determined to have strong lipo-solubility when 1 g Kow≥3.5, and then step S3 for microbial drug resistance assessment was carried out for further assessment, as shown in appendix 1:

S2-2, determination of antibiotic environment concentration: the environment concentration MEC of the target antibiotic or target antibiotic derivative was measured, the target antibiotic or target antibiotic derivative had a sustained input source when the environment concentration MEC≥10, and then step S3 for microbial drug resistance assessment was carried out for further assessment;

S3, microbial drug resistance assessment: the drug resistance risk of microbial flora in the target watershed was characterized by using drug resistance risk quotient value $RQ_R$, which was represented by the following formula:

$$RQ_R = MEC/PNEC_R;$$

in the formula, MEC was the environment concentration of the target antibiotic or target antibiotic derivative measured in step S2-2, $PNEC_R$ was drug resistance prediction invalid concentration of microbial flora in the target watershed, which was represented by the following formula:

$$PNEC_R = MIC/AF;$$

in the formula, MIC was a minimum inhibitory concentration of microbial flora in the target watershed, AF was a dimensionless assessment factor which was 10, the minimum inhibitory concentration MIC of the microbial flora in the target watershed was determined by EUCAST database, thereby obtaining the drug resistance prediction invalid concentration $PNEC_R$ of the microbial flora in the target watershed, as shown in appendix 2;

the drug resistance risk level of the microbial flora in the target watershed was divided into 4 grades according to the size of $RQ_R$ value: no risk was $RQ_R<0.01$, low risk was $0.01<RQ_R<0.1$, medium risk was $0.1<RQ_R<1$ and high risk was $RQ_R>1$, the drug resistance risk level of the microbial flora in the target watershed was high when $RQ_R>0.1$, and then step S4 for high-level assessment was carried out for further assessment, or else the assessment was terminated;

S4, high-level assessment:

S4-1, extraction of environmental microbes: 50 weight parts of water samples in the target watershed were collected and then filtered through a filter membrane with a pore diameter of 0.25 μm, the filter membrane was cut into fragments with an area of 20 mm² after filtration, the fragments together with a phosphate buffer solution that was 1.3 times of the fragments in volume were put into a container, wherein the phosphate buffer solution comprised 10 g/L of NaCl solution, 0.25 g/L of KCl solution, 1.6 g/L of $Na_2HPO_4$ solution, 0.3 g/L of $KH_2PO_4$ solution and the balance of water, the pH of the phosphate buffer solution was 7.4, and then glass beads that were 2.8 times of the fragments in volume were added into the container, vortex oscillation was carried out for 18 min, and then the filter membrane and the glass beads were removed by filtration to obtain bacterial solution supernatant for later use;

S4-2, gradient concentration culture of antibiotics: the bacterial solution supernatant obtained in step S4-1 was respectively added into 5 sterilized conical flasks, each sterilized conical flask contained 2.7 weight parts of bacterial solution supernatant, 3 glass slides were put into each conical flask for stimulating biological membrane development of sediments, 0.4 weight part of LB culture medium containing 10 g/L of tryptone, 5 g/L of yeast powder, 10 g/L of sodium chloride and the balance of water was added, and then target antibiotics or target antibiotic derivatives with different concentrations that were 0, 0.01 μg/L, 0.1 μg/L, 1 μg/L, 10 μg/L and 100 μg/L respectively were added into 5 different sterilized conical flasks, and then oscillatory reaction was carried out for 14 days at room temperature of 30° C. to obtain a target solution;

S4-3, DNA extraction: target solution DNA in the target solution obtained in step S4-2 was extracted while collecting bacteria on the glass slides in the sterilized conical flasks to the phosphate buffer solution to extract bacterial DNA;

S4-4, determination of resistant genes: resistant genes corresponding to the target antibiotics or target antibiotic derivatives were determined, 2-20 resistant genes were taken, and the maximum value was taken if there were less than 20, as shown in appendix 3. The abundance of the target solution DNA or bacterial DNA was determined to calculate the average relative abundance P of the resistant gene, and meanwhile the average relative abundance $P_0$ of the resistant gene before step S4 was calculated, and selectivity coefficient S was calculated, which was represented by the following formula:

$$S=ln(P/P_0)$$

S4-5, model fitting: antibiotic concentration C was taken as a horizontal ordinate, and the selectivity coefficient S corresponding to the target solution DNA or bacterial DNA was taken as a longitudinal ordinate, and fitting was performed by using logistic model. When S=0, the corresponding antibiotic concentration C was the MSC value. The MSC values of the target solution DNA or bacterial DNA were compared, and the smaller MSC value was taken as control basis. This MSC value indicated that microbes carrying drug-resistant genes could not be enriched under antibiotic conditions being higher than the antibiotic concentration C, so that the relative abundance of drug-resistant genes in the microbial flora was increased.

Example 2

This example was different from example 1 in that:
The target watershed was sea area.

Example 3

This example was different from example 1 in that:
The target watershed was a water function area, such as reservoir.

Example 4

This example was different from example 1 in that:
the microbial flora in the step S3 was fungi.

Example 5

This example was different from example 1 in that:
the microbial flora in the step S3 was *Actinomyces*.

Example 7

This example was different from example 1 in that:
the step S3 further comprised environment persistence assessment: the half-life period $t_{1/2}$ of the target antibiotics or target antibiotic derivatives was obtained by using database querying combined with model prediction, an environment persistence level was divided into 3 grades according to the size of the half-life period $t_{1/2}$: non persistence was $t_{1/2}<60d$, persistence was $60d<t_{1/2}<180d$, and high persistence was $t_{1/2}>180d$; when $t_{1/2}>60$, the target antibiotics or target antibiotic derivatives had environment persistence, so regardless of the drug resistance risk $RQ_R$ value of the microbial flora in the target watershed, step S4 was carried out for further assessment, as shown in appendix 4.

Example 8

This example was different from example 1 in that:
S4-1, extraction of environmental microbes: 50 weight parts of water samples in the target watershed were collected and then filtered through a filter membrane with a pore diameter of 0.2 μm, the filter membrane was cut into fragments with an area of 15 mm² after filtration, the fragments were put into a container and phosphate buffer solution that was 1.2 times of the fragments in volume was added, wherein the phosphate buffer solution comprised 10 g/L of NaCl solution, 0.25 g/L of KCl solution, 1.6 g/L of $Na_2HPO_4$ solution, 0.3 g/L of $KH_2PO_4$ solution and the balance of water, the pH of the phosphate buffer solution was 7.4, and then glass beads that were 2.5 times of the fragments in volume were added into the container, vortex oscillation was carried out for 15 min, and then the filter membrane and the glass beads were removed by filtration to obtain bacterial solution supernatant for later use;

S4-2, gradient concentration culture of antibiotics: the bacterial solution supernatant obtained in step S4-1 was respectively added into 6 sterilized conical flasks, each sterilized conical flask contained 2.5 weight parts of bacterial solution supernatant, 3 glass slides were put into each conical flask for stimulating biological membrane development of sediments, 0.2 weight part of LB culture medium containing 10 g/L of tryptone, 5 g/L of yeast powder, 10 g/L of sodium chloride and the balance of water was added, and then target antibiotics or target antibiotic derivatives with different concentrations that were 0, 0.01 μg/L, 0.1 μg/L, 1 μg/L, 10 μg/L and 100 μg/L respectively were added into 6 different sterilized conical flasks, and then oscillatory reaction was carried out for 14 days at room temperature of 28° C. to obtain a target solution.

Example 9

This example was different from example 1 in that:

S4-1, extraction of environmental microbes: 50 weight parts of water samples in the target watershed were collected and then filtered through a filter membrane with a pore diameter of 0.3 μm, the filter membrane was cut into fragments with an area of 28 mm² after filtration, the fragments were put into a container and phosphate buffer solution that was 1.5 times of the fragments in volume is added, wherein the phosphate buffer solution comprised 10 g/L of NaCl solution, 0.25 g/L of KCl solution, 1.6 g/L of $Na_2HPO_4$ solution, 0.3 g/L of $KH_2PO_4$ solution and the balance of water, pH of the phosphate buffer solution was 7.4, and then glass beads that were 3 times of the fragments in volume were added into the container, vortex oscillation was carried out for 20 min, and then the filter membrane and the glass beads were removed by filtration to obtain bacterial solution supernatant for later use;

S4-2, gradient concentration culture of antibiotics: the bacterial solution supernatant obtained in step S4-1 was respectively added into 6 sterilized conical flasks, each sterilized conical flask contained 3 weight parts of bacterial solution supernatant, 3 glass slides were put into each conical flask for stimulating biological membrane development of sediments, 0.5 weight part of LB culture medium containing 10 g/L of tryptone, 5 g/L of yeast powder, 10 g/L of sodium chloride and the balance of water was added, and then target antibiotics or target antibiotic derivatives with different concentrations that were 0, 0.01 μg/L, 0.1 μg/L, 1 μg/L, 10 μg/L and 100 μg/L respectively were added into 6 different sterilized conical flasks, and then oscillatory reaction was carried out for 14 days at room temperature of 33° C. to obtain a target solution.

Experimental Example

Figure 2:
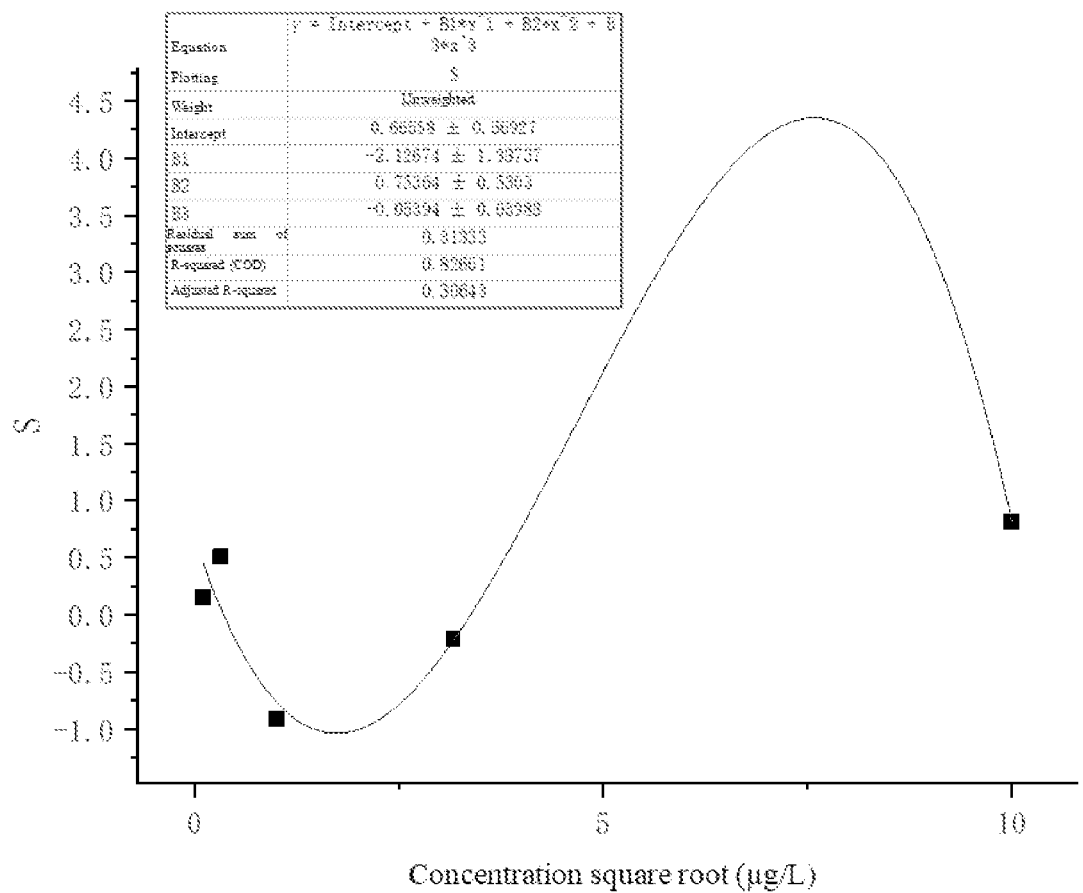
FIG. 2 is a diagram showing relative abundance and antibiotic drug-resistant gene concentration in experimental examples according to the present disclosure.

By taking method parameters in example 1 as an example, the target antibiotic was tetracycline. A graph showing a corresponding relationship between the concentration of the obtained target antibiotic and the selectivity coefficient S is shown in FIG. 2. The average relative abundance P of the resistant gene was calculated by using the abundance of the target solution DNA of the target antibiotic. Specific parameters are seen in Table 1.

TABLE 1

Corresponding relationship between concentration and selectivity coefficient of tetracycline
Example 1: tetracycline

| Concentration μg/L | Average relative abundance $P_0$ before experiment | Average relative abundance P after experiment | Selectivity coefficient S |
|---|---|---|---|
| 0.01 | 0.6 | 0.7 | 0.15 |
| 0.1 | 1 | 1.66 | 0.51 |
| 1 | 0.7 | 0.28 | −0.91 |
| 10 | 0.5 | 0.4 | −0.21 |
| 100 | 0.6 | 1.35 | 0.81 |

By combining FIG. 1 and FIG. 2, it can be seen that the MSC value of the target antibiotic tetracycline, i.e., the corresponding antibiotic concentration at S=0 is about $3.375^2=11.39$ μg/L. Therefore, microbes carrying drug-resistant genes can be enriched under antibiotic conditions being higher than a tetracycline concentration of 11.39 μg/L. Parameter adjustments in examples 2-9 are all conventional adjustments in the present disclosure. Within the parameter variation range given in the present disclosure, all experimental parameters in examples 2-9 can achieve the assessment method of the present disclosure.

APPENDIX 1

| Category | Antibiotics | log kow |
|---|---|---|
| Sulfonamides | Acetylsulfonamide | −0.604 |
| | Sulfamethazine | 0.933 |
| | Sulfabenzamide | 1.30 |
| | Sulfadimethoxazole | 1.03 |
| | Sulfadiazine | −0.090 |
| | Sulfamoxole | 1.03 |
| | Sulfasalazine | 0.350 |
| | Sulfachloropyridazine | 0.310 |
| | Sulfamethoxydiazine | 0.410 |
| | Sulfamethoxypyridazine | 0.320 |
| Quinolones | Flumequine | 1.60 |
| | Oxolinic acid | 0.940 |
| | Enrofloxacin | 0.700 |
| | Norfloxacin | −1.03 |
| | Ofloxacin | −0.39 |
| | Marbofloxacin | −2.92 |
| | Cinoxacin | 1.59 |
| | Ciprofloxacin | −0.00080 |
| | Lomefloxacin | 0.312 |
| | Fleroxacin | 0.046 |
| | Pefloxacin | −0.095 |
| Macrolides | Azithromycin | 4.02 |
| | Roxithromycin | 2.75 |
| | Erythromycin | 3.06 |
| | Dehydrated erythromycin | 4.34 |
| | Clarithromycin | 3.16 |
| | Spiramycin | 1.88 |
| | Tylosin | 1.05 |
| Lincomycins | Clindamycin | 2.16 |
| | Lincomycin | 0.290 |
| Tetracyclines | Oxytetracycline | −2.87 |
| | Tetracycline | −1.33 |
| | Doxycycline | −1.18 |
| | Lodermycin | −1.14 |
| | Chlorquatrimycin | 0.330 |

APPENDIX 2

Minimum inhibitory concentration (MIC) of some antibiotics and drug resistance prediction invalid concentration (PNECr) of microbes

| Antibiotics | Observed MIC | PNECr |
|---|---|---|
| Amikacin | 250 | 25 |
| Amoxicillin | 4 | 0.4 |
| Amoxicillin-clavulanic acid (mixed at will) | 1000 | 100 |
| Amphotericin B | 8 | 0.8 |
| Ampicillin | 4 | 0.4 |
| Ampicillin-sulbactam sodium (mixed at will) | 500 | 50 |
| Ampicillin-sulbactam sodium (mixed in a ratio) | 125 | 12.5 |
| Anidurafenkin | 2 | 0.2 |
| Avilamycin | 1000 | 100 |
| Azithromycin | 16 | 1.6 |
| Aztreonam | 32 | 3.2 |
| Bacitracin | 2000 | 200 |
| Penicillin | 4 | 0.4 |
| Capreomycin | 1000 | 100 |
| Cefaclor | 32 | 3.2 |
| Cefadroxil | 125 | 12.5 |
| Cefalexin | 250 | 25 |

-continued

| Antibiotics | Observed MIC | PNECr |
|---|---|---|
| Cefoperazone | 2000 | 200 |
| Cefoxitin | 64 | 6.4 |
| Cefazolin | 32 | 3.2 |
| Cefdinir | 32 | 3.2 |
| Cefepime | 8 | 0.8 |
| Clavulanic acid-cefepime proxetil | 1000 | 100 |
| Cefixime | 4 | 0.4 |
| Cefoperazone | 16 | 1.6 |
| Cefotaxime | 2 | 0.2 |
| Clavulanic acid-cefepime proxetil | 8 | 0.8 |
| Cefoxitin | 250 | 25 |
| Cefpirome | 4 | 0.4 |
| Cefpodoxime | 8 | 0.8 |
| Cefpodoxime-clavulanic acid | 250 | 25 |
| Ceftazidime | 16 | 1.6 |
| Clavulanic acid-ceftazidime | 8 | 0.8 |
| Ceftibuten | 8 | 0.8 |
| Ceftiofur | 8 | 0.8 |
| Ceftobiprole | 4 | 0.4 |
| Ceftriaxone | 2 | 0.2 |
| Cefuroxime | 8 | 0.8 |
| Chloramphenicol | 125 | 12.5 |
| Ciprofloxacin | 2 | 0.2 |
| Clarithromycin | 8 | 0.8 |
| Clarithromycin | 32,000 | 3200 |
| Clinafloxacin | 32 | 3.2 |
| Clindamycin | 16 | 1.6 |
| Cloxacillin | 64 | 6.4 |
| Colistin | 64 | 6.4 |
| Daptomycin | 32 | 3.2 |
| Doripenan | 2 | 0.2 |
| Doxycycline | 32 | 3.2 |
| Enrofloxacin | 8 | 0.8 |
| Ertapenem | 2 | 0.2 |
| Erythromycin | 16 | 1.6 |
| Ethambutol | 1000 | 100 |
| Faropenem | 8 | 0.8 |
| Fidaxomicin | 8 | 0.8 |
| FLORFENICOL | 125 | 12.5 |
| Fluconazol | 64 | 6.4 |
| Flumequine | 64 | 6.4 |
| Fosfomycin | 125 | 12.5 |
| Fusiform acid | 32 | 3.2 |
| Gatifloxacin | 4 | 0.4 |
| Difloxacin | 2 | 0.2 |
| Gentamicin | 16 | 1.6 |
| Imipenem | 2 | 0.2 |
| Isoniazide | 64 | 6.4 |
| Itraconazole | 4 | 0.4 |
| Kanamycin | 125 | 12.5 |
| Ketoconazole | 4 | 0.4 |
| Levofloxacin | 4 | 0.4 |
| Lincomycin | 500 | 50 |
| Linezolid | 125 | 12.5 |
| Lolakabiv | 125 | 12.5 |
| Messilinan | 64 | 6.4 |
| MeropeneM | 2 | 0.2 |
| Metronidazole | 16 | 1.6 |
| Mikafenjin | 4 | 0.4 |
| Minocycline | 32 | 3.2 |
| Moxifloxacin | 2 | 0.2 |
| Mupirocin | 32 | 3.2 |
| Nalidixic acid | 500 | 50 |
| Narasin | 125 | 12.5 |
| Neomycin | 125 | 12.5 |
| Netilmicin | 16 | 1.6 |
| Furantoin | 4000 | 400 |
| Norfloxacin | 16 | 1.6 |
| Ofloxacin | 8 | 0.8 |
| Oxacillin | 32 | 3.2 |
| Oxytetracycline | 125 | 12.5 |
| Pefloxacin | 4000 | 400 |
| Phenoxymethylpenicillin | 4 | 0.4 |
| Piperacillin | 4 | 0.4 |
| Piperacillin tazobactam | 8 | 0.8 |
| Quinupustine | 4 | 0.4 |
| Retapamulin | 64 | 6.4 |

-continued

| Antibiotics | Observed MIC | PNECr |
|---|---|---|
| Rifampicin | 8 | 0.8 |
| Roxithromycin | 2 | 0.2 |
| Secnidazole | 32 | 3.2 |
| Sparfloxacin | 500 | 50 |
| Spectinomycin | 2 | 0.2 |
| Spiramycin | 2000 | 200 |
| Streptomycin | 125 | 12.5 |
| Sulbactam sodium | 250 | 25 |
| Sulfamethoxazole | 1000 | 100 |
| Teicoplanin | 1000 | 100 |
| Telithromycin | 16 | 1.6 |
| Tetracycline | 16 | 1.6 |
| Thiamphenicol | 500 | 50 |
| Tiamulin | 500 | 50 |
| Ticarcillin | 250 | 25 |
| Ticarcillin clavulanic acid | 64 | 6.4 |
| Tigecycline | 16 | 1.6 |
| Tilmicosin | 250 | 25 |
| Tobramycin | 16 | 1.6 |
| Trimethoprim | 16 | 1.6 |
| Trimethoprim sulfamethoxazole | 8 | 0.8 |
| Travafloxacin | 8 | 0.8 |
| Tylosin | 2000 | 200 |
| Vancomycin | 125 | 12.5 |
| Viomycin | 1000 | 100 |
| Virginiamycin | 250 | 25 |
| Voriconazole | 2 | 0.2 |

APPENDIX 3

Types of resistant genes corresponding to antibiotics

| Antibiotics | Resistant genes |
|---|---|
| Aminoglycosides | AC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), and APH(9) |
| β-lactams | AER, BLA1, CTX-M, KPC, SHV, TEM, BlaB, CcrA, IMP, NDM, VIM, ACT, AmpC, CMY, LAT, PDC, OXA, blaI, blaR1, mecI, and mecR1 |
| β-lactams | CmlA, and cmxA |
| Sulfonamides | dfrA1, dfrA12, folA, sul1, sul2, sulA/folP, and sulA/folP |
| Tetracyclines | Tet(32), tet(34), tet(35), tet(36), tet(37), tet(38), tetA, tetB, tetC, tetD, tetE, tetG, tetH, tetJ, tetK, tetL, tetM, tetO, tetPA, tetPB, tetQ, tetR, tetS, tetT, tetU, tetV, tetW, and tetX |
| Vancomycin | vanA, vanB, vanC, vanC1, vanG, vanHB, vanHD, vanRA, vanRB, vanRC, vanRD, vanSA, vanSB, vanSC, vanSE, vanTC, vanTE, vanTG, vanWB, vanWG, vanXA, vanXB, anXD, vanYB, and vanYD |
| Quinolones | GyrA, GyrB, ParC, qnrA, qnrB, qnrC, qnrS, qnrO, and qnrW |
| Erythromycin, Lincomycin, and streptomycin | ereA, erm(34), erm(35), erm(36), ermA, ermA/ermTR, ermB, ermC, ermF, ermJ/ermD, ermK-01, ermT-01, ermT-02, ermX, ermY, lmrA-01, lnuA-01, lnuB-01, lnuB-02, lnuC, matA/mel, mdtA, mefA, mphA-01, mphA-02, mphB, |

-continued

| Antibiotics | Resistant genes |
|---|---|
| | mphC, msrA-01, msrC-01, oleC, pikR1, pikR2, vatB-01, vatB-02, vatC-01, vatC-02, vatD, vatE-01, vatE-02, vgaA-01, vgaA-02, vgaB-01, vgaB-02, vgb-01, vgbB-01, and vgbB-02 |

APPENDIX 4

Half-life period of some antibiotics in water

| Category | Antibiotics | $t_{1/2}$ (h) | Sources |
|---|---|---|---|
| Sulfonamides | Sulfadiazine | 9.00E+02 | Literatures |
| | Sulfamethazine | 8.72E+02 | Literatures |
| | Acetylsulfonamide | 9.00E+02 | Literatures |
| | Sulfamethoxazole | 5.29E+02 | Literatures |
| | Sulfathiazole | 9.12E+02 | Literatures |
| | Sulfachloropyridine | 1.44E+03 | Model calculation |
| | Sulfamethoxydiazine | 9.00E+02 | Model calculation |
| | Sulfamethizole | 9.00E+02 | Model calculation |
| | Sulfamethazine | 9.00E+02 | Model calculation |
| | Sulfabenzamide | 9.00E+02 | Model calculation |
| | Sulfamethoxypyridazine | 9.00E+02 | Model calculation |
| | Sulfadimoxine | 9.00E+02 | Model calculation |
| | Sulfadimethoxypyrimidine | 9.00E+02 | Model calculation |
| | Sulfadimethisoxazol | 9.00E+02 | Model calculation |
| | Sulfamonomethoxine | 9.00E+02 | Model calculation |
| | Sulphaguanidine | 9.00E+02 | Model calculation |
| | Sulfaquinoxaline | 9.00E+02 | Model calculation |
| | Trimethoprim | 1.44E+03 | Literatures |
| Quinolones | Norfloxacin | 1.44E+03 | Model calculation |
| | Ciprofloxacin | 1.44E+03 | Literatures |
| | Ofloxacin | 1.20E+02 | Literatures |
| | Lomefloxacin | 4.32E+03 | Model calculation |
| | Enrofloxacin | 4.32E+03 | Literatures |
| | Fleroxacin | 4.32E+04 | Model calculation |
| | Pefloxacin | 4.32E+03 | Model calculation |
| | Difloxacin | 4.32E+04 | Literatures |
| | Marbofloxacin | 1.44E+03 | Model calculation |
| | Enoxacin | 4.32E+03 | Model calculation |
| Macrolides | Clarithromycin | 4.32E+03 | Model calculation |
| | Spiramycin | 4.32E+03 | Model calculation |
| | Azithromycin | 4.32E+03 | Model calculation |
| | Spiramycin | 4.32E+03 | Model calculation |
| | Erythromycin | 4.32E+03 | Model calculation |
| | Roxithromycin | 4.32E+03 | Literatures |
| | Tylosin | 2.42E+03 | Literatures |
| | Dehydrated erythromycin | 8.76E+03 | Literatures |
| Lincomycins | Lincomycin | 9.00E+02 | Model calculation |
| | Clindamycin | 1.44E+03 | Model calculation |
| Tetracyclines | Oxytetracycline | 2.16E+02 | Literatures |
| | Tetracycline | 7.20E+01 | Literatures |
| | Aureomycin | 4.32E+03 | Model calculation |
| | Doxycycline | 1.44E+03 | Model calculation |
| | Methacycline | 1.44E+03 | Model calculation |
| β-lactams | Cefalexin | 9.00E+02 | Model calculation |
| | Amoxicillin | 9.00E+02 | Model calculation |
| | Penicillin | 9.00E+02 | Model calculation |
| | Cefazolin | 9.00E+02 | Model calculation |
| Others | Ormetoprim | 1.44E+03 | Model calculation |
| | Florfenicol | 1.44E+03 | Model calculation |
| | Chloramphenicol | 1.44E+03 | Model calculation |
| | Armillarisin | 1.44E+03 | Model calculation |

The invention claimed is:

1. A method for assessing microbial drug resistance multi-level risks of antibiotic residues in water environment, comprising the following steps:

S1, environment monitoring:

S1-1: background survey on production, use and emission of antibiotics in a target watershed is carried out, a target antibiotic monitoring list is established for ecological risk assessment, and environment monitoring of target antibiotics is then carried out;

S1-2: target antibiotic derivative monitoring is carried out on the target watershed, a target antibiotic derivative monitoring list also needs to be established if byproduct reaction or biotransformation of target antibiotics occurs, and then environment monitoring of target antibiotic derivatives is carried out;

S2, preliminary screening of antibiotics: the target antibiotics of the target watershed obtained in step S1-1 and the target antibiotic derivatives of the target watershed obtained in step S1-2 are preliminarily screened, step S3 for microbial drug resistance assessment is carried out for further assessment if any one of S2-1 to S2-2 is met;

S2-1, determination of n-octanol/water partition coefficient: the n-octanol/water partition coefficient (Kow) of the target antibiotic or target antibiotic derivative is calculated, and the logarithmic value of the calculated n-octanol/water partition coefficient with a base of 10 is calculated, the target antibiotic or target antibiotic derivative has strong liposolubility when 1 g Kow≥3.5, and then step S3 for microbial drug resistance assessment is carried out for further assessment;

S2-2, determination of antibiotic environment concentration: the environment concentration (MEC) of the target antibiotic or target antibiotic derivative is measured, the target antibiotic or target antibiotic derivative has a sustained input source when MEC≥10, and then step S3 for microbial drug resistance assessment is carried out for further assessment;

S3, assessment of microbial drug resistance: the drug resistance risk of microbial flora in the target watershed is characterized by using drug resistance risk quotient value (RQr) which is represented by the following formula:

$(RQr)=MEC/PNECr;$ in the formula, MEC is the environment concentration of the target antibiotic or target antibiotic derivative measured in step S2-2, PNECr is a drug resistance prediction invalid concentration of microbial flora in the target watershed, which is represented by the following formula:

$PNECr=MIC/AF;$ in the formula, MIC is the minimum inhibitory concentration of microbial flora in the target watershed, AF is a dimensionless assessment factor, MIC of the microbial flora in the target watershed is determined by European Union Committee on Antimicrobial Susceptibility Testing (EUCAST) database, thereby obtaining PNECr of the microbial flora in the target watershed;

the drug resistance risk level of the microbial flora in the target watershed is divided into 4 grades according to the size of (RQr) value: no risk is (RQr)<0.01, low risk is 0.01<(RQr)<0.1, medium risk is 0.1<(RQr)<1 and high risk is (RQr)>1, the drug resistance risk level of the microbial flora in the target watershed is high when (RQr)>0.1, and then step S4 for high-level assessment is carried out for further assessment;

S4, high-level assessment:

S4-1, extraction of environmental microbes: 50 weight parts of water samples in the target watershed are collected and then filtered through a filter membrane, the filter membrane is cut into fragments with an area of 15-28 mm$^2$ after filtration, the fragments together with a phosphate buffer solution that is 1.2-1.5 times of the fragments in volume are put into a container, and then glass beads that are 2.5-3 times of the fragments in volume are added into the container, vortex oscillation is carried out for 15-20 min, and then the filter membrane and the glass beads are removed by filtration to obtain bacterial solution supernatant for later use;

S4-2, gradient concentration culture of antibiotics: the bacterial solution supernatant obtained in step S4-1 is respectively added into 5-6 sterilized conical flasks, 3 glass slides are put into each conical flask for stimulating biological membrane development of sediments, 0.2-0.5 weight part of LB culture medium is added, and then target antibiotics or target antibiotic derivatives with different concentrations that are 0, 0.01 µg/L, 0.1 µg/L, 1 µg/L, 10 µg/L and 100 µg/L respectively are added into the 5-6 different sterilized conical flasks, and then oscillatory reaction is carried out for 14 days at room temperature of 28-33° C. to obtain a target solution;

S4-3, DNA extraction: DNA in the target solution obtained in step S4-2 is extracted while collecting bacteria on the glass slides in the sterilized conical flasks to the phosphate buffer solution to extract bacterial DNA;

S4-4, determination of resistant genes: resistant genes corresponding to the target antibiotics or target antibiotic derivatives are determined, the abundance of the target solution DNA or bacterial DNA is determined to calculate the average relative abundance (P) of the resistant genes, and meanwhile the average relative abundance $P_0$ of the resistant genes before step S4 is calculated, and selectivity coefficient (S) is calculated, which is represented by the following formula:

$S=In(P/P_0)$

S4-5, model fitting: the antibiotic concentration (C or MSC) is taken as a horizontal ordinate, and the selectivity coefficient (S) corresponding to the target solution DNA or bacterial DNA is taken as a longitudinal ordinate, and fitting is carried out by using logistic model, when S=0, the corresponding antibiotic concentration is MSC value, the MSC values of the target solution DNA or bacterial DNA are compared, and the smaller MSC value is taken as control basis, the MSC value indicates that microbes carrying drug-resistant genes cannot be enriched under antibiotic conditions being higher than the antibiotic concentration, so that the relative abundance of drug-resistant genes in the microbial flora is increased.

2. The method for assessing microbial drug resistance multi-level risks of antibiotic residues in water environment according to claim 1, wherein the target watershed includes a river basin, a sea area and a reservoir.

3. The method for assessing microbial drug resistance multi-level risks of antibiotic residues in water environment according to claim 1, wherein the microbial flora in the step S3 includes bacteria, fungi or *Actinomyces*.

4. The method for assessing microbial drug resistance multi-level risks of antibiotic residues in water environment according to claim 1, wherein the step S3 further comprises environment persistence assessment: the half-life period $t_{1/2}$ of the target antibiotics or target antibiotic derivatives is obtained by database querying combined with model prediction, an environment persistence level is divided into 3 grades according to the size of the half-life period $t_{1/2}$: non persistence is $t_{1/2}<60d$, persistence is $60d<t_{1/2}<180d$, and high persistence is $t_{1/2}>180d$; when $t_{1/2}>60$, the target antibiotics or target antibiotic derivatives have environment persistence, so regardless of the drug resistance risk RQr value of the microbial flora in the target watershed, step S4 is carried out for further assessment.

5. The method for assessing microbial drug resistance multi-level risks of antibiotic residues in water environment according to claim 1, wherein the pore diameter of the filter membrane in the step S4-1 is 0.2-0.3 μm.

6. The method for assessing microbial drug resistance multi-level risks of antibiotic residues in water environment according to claim 1, wherein the phosphate buffer solution in the step S4-4 and S4-3 comprises 10 g/L of NaCl solution, 0.25 g/L of KCl solution, 1.6 g/L of $Na_2HPO_4$ solution, 0.3 g/L of $KH_2PO_4$ solution and the balance of water, and the pH of the phosphate buffer solution is 7.4.

7. The method for assessing microbial drug resistance multi-level risks of antibiotic residues in water environment according to claim 1, wherein the LB culture medium in the step S4-1 comprises 10 g/L of tryptone, 5 g/L of yeast powder, 10 g/L of sodium chloride and the balance of water.

8. The method for assessing microbial drug resistance multi-level risks of antibiotic residues in water environment according to claim 1, wherein in the step S4-4, 2-20 resistant genes are selected.

9. The method for assessing microbial drug resistance multi-level risks of antibiotic residues in water environment according to claim 1, wherein in the step S3, the dimensionless assessment factor (AF) is 10.

\* \* \* \* \*